United States Patent [19]
Kohrs et al.

[11] Patent Number: 5,609,636
[45] Date of Patent: Mar. 11, 1997

[54] SPINAL IMPLANT

[75] Inventors: Douglas W. Kohrs, Edina, Minn.;
Hansen A. Yuan, Fayetteville, N.Y.;
David W. Stassen, Edina, Minn.

[73] Assignee: Spine-Tech, Inc., Minneapolis, Minn.

[21] Appl. No.: 585,297

[22] Filed: Jan. 11, 1996

Related U.S. Application Data

[63] Continuation-in-part of Ser. No. 247,857, May 23, 1994, abandoned.

[51] Int. Cl.$^6$ ............................................. A61F 2/44
[52] U.S. Cl. ................................. 623/17; 606/61
[58] Field of Search ................. 623/16, 17, 20; 606/60, 61

[56] References Cited

U.S. PATENT DOCUMENTS

| | | |
|---|---|---|
| 2,677,369 | 5/1954 | Knowles . |
| 4,349,921 | 9/1982 | Kuntz . |
| 4,501,269 | 2/1985 | Bagby . |
| 4,743,256 | 5/1988 | Brantigan . |
| 4,834,757 | 5/1989 | Brantigan . |
| 4,878,915 | 11/1989 | Brantigan . |
| 4,936,848 | 6/1990 | Bagby et al. . |
| 4,961,740 | 10/1990 | Ray et al. . |
| 5,015,247 | 5/1991 | Michelson . |
| 5,026,373 | 6/1991 | Ray et al. . |
| 5,055,104 | 10/1991 | Ray . |
| 5,062,850 | 11/1991 | MacMillan . |
| 5,192,327 | 3/1993 | Brantigan . |
| 5,294,391 | 3/1994 | McMillin . |
| 5,489,307 | 2/1996 | Kuslich et al. ........... 623/17 |

OTHER PUBLICATIONS

International Publication No. WO94/17759 dated Aug. 18, 1994, on PCT Application No. PCT/US94/00586.
International Search Report of International Application No. PCT/US95/01655.

*Primary Examiner*—Robert A. H. Clarke
*Attorney, Agent, or Firm*—Merchant, Gould, Smith, Edell, Welter & Schmidt

[57] ABSTRACT

An implant for use in spinal stabilization includes four generally linear thread segments. The thread segments are maintained and spaced apart alignment by rigid supports. The thread segments include a plurality of individual threads with the individual threads of the segments defining a thread pattern. The supports and the thread segments define a hollow implant interior exposed to an exterior of the implant.

13 Claims, 15 Drawing Sheets

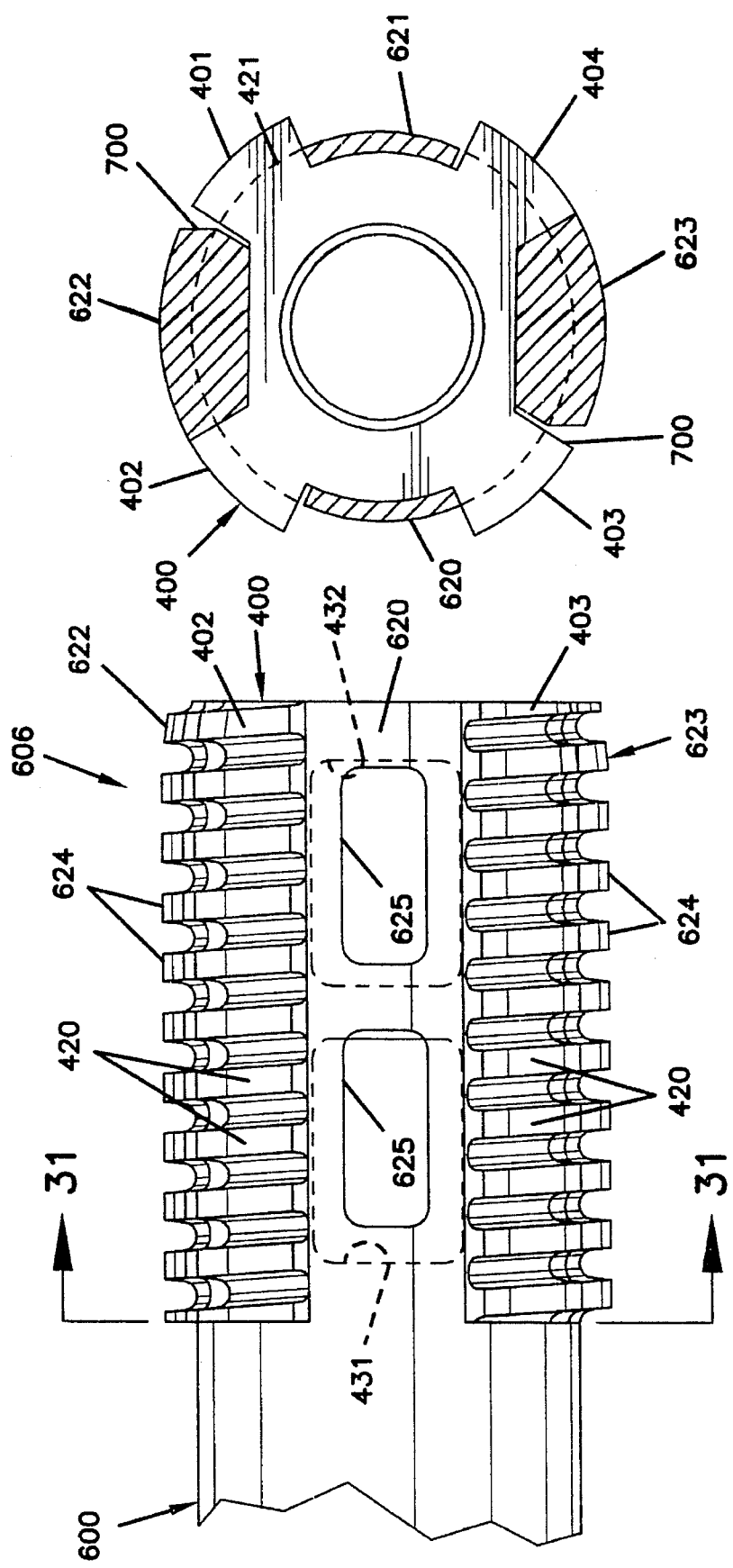

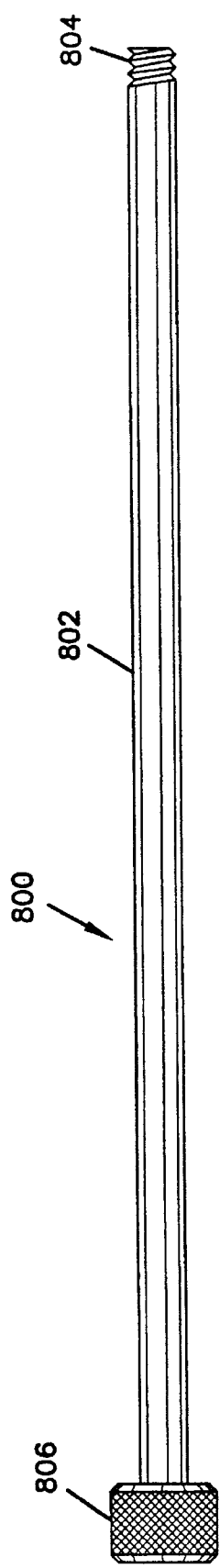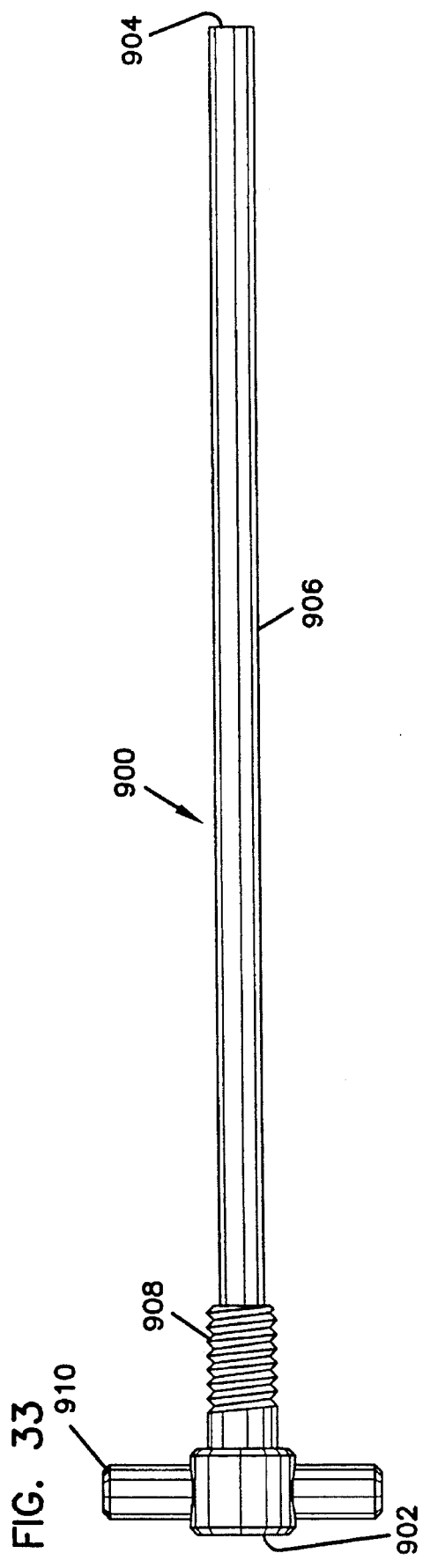
FIG. 32
FIG. 33

SPINAL IMPLANT

CROSS REFERENCE TO RELATED APPLICATION

The present application is a continuation-in-part of U.S. patent application Ser. No. 08/247,857 filed May 23, 1994, and entitled "INTERVERTEBRAL FUSION IMPLANT" now abandoned.

BACKGROUND OF THE INVENTION

1. Field of the Invention

This invention pertains to intervertebral fusion. More particularly, this invention pertains to an implant to facilitate fusion between two vertebrae.

2. Description of the Prior Art

Back pain is extremely debilitating. Individuals suffering from severe back pain are frequently precluded from the full enjoyment of life including gainful employment and leisure activities. In addition to the substantial human costs associated with back pain, society bears a substantial financial cost. Lost employment time adversely impacts on productivity as does medical insurance costs.

Frequently, the cause of back pain is traceable to diseased disc material between opposing vertebrae. When the disc material is diseased, the opposing vertebrae are not adequately supported.

In order to address back pain resulting from disc disease, prior art surgical techniques have been developed to fuse the opposing vertebrae. Such techniques include removing the diseased disc and packing the disc space with bone. The intent of such a procedure is for the packed bone to grow together and fuse with the bone of the opposing vertebra. If successful, the two opposing vertebrae are now rigidly linked thereby avoiding intervertebral instability.

In fusing opposing vertebrae, the prior art has developed surgical techniques and apparatus to facilitate interbody fusion as well as to permit stabilization of the vertebra while the fusion process is occurring. To this end, surgical implants have been developed.

An example of a surgical implant for facilitating interbody fusion is shown in U.S. Pat. No. 5,015,247 to Michelson dated May 14, 1991. Michelson uses a circular cross-section cylindrical implant which is of uniform diameter throughout its length and which includes an external thread. The implant is hollow and has holes formed through the cylindrical wall of the implant. The implant is placed within a prepared site between the vertebrae. The prepared site is a bore formed through the disc material as well as partially formed through the end plates of the opposing vertebrae. The implant is threaded into the bore and packed with bone chips or the like.

Another example of an interbody fusion device is shown U.S. Pat. No. 4,834,757 to Brantigan dated May 30, 1989. The Brantigan device is a parallelepiped plug which is forced into a complementarily shaped cavity formed between opposing vertebrae.

Prior art interbody fusion devices are not trouble free. For example, prior art devices suffer from uncontrolled subsidence of the device into the vertebral body. By subsidence, it is meant that after the implant is placed between the opposing vertebra, the implant migrates into the vertebral body. Also, in many prior art implants, direct bone apposition only occurs on two surfaces. In addition, unwanted invasion of disc or cartilage material into the implant may occur upon insertion. Such prior art devices typically have minimal surface area contact with the end plates of the vertebra. In addition to the above, such prior art devices have a geometry which prevents close placement when two implants are placed in a side-by-side relation within a common disc space. A prior art device to increase the density of implant placement is shown in U.S. Pat. No. 5,055,104 to Ray dated Oct. 8, 1991. In that patent, the device is a helical thread. Two such devices are placed side-by-side with the threads intermeshing.

It is an object of the present invention to provide an implant for use in interbody fusion. It is a further object of the present invention to provide such an implant which has reduced subsidence.

SUMMARY OF THE INVENTION

According to a preferred embodiment of the present invention, an implant is provided for facilitating intervertebral fusion between opposing vertebrae. The implant includes four generally linear thread segments. The thread segments are held in alignment and spaced apart by rigid supports. The thread segments include a plurality of individual threads which define a thread pattern. The supports and the thread segments define a hollow implant interior exposed to an exterior of the implant.

BRIEF DESCRIPTION OF THE DRAWINGS

FIG. 30 is an enlarged side elevation view of an insertion tool receiving the implant of FIG. 17;

FIG. 31 is a view taken along lines 31—31 of FIG. 30;

FIG. 32 is a side elevation view of a first insert for the insertion tool of FIG. 24; and FIG. 33 is a second insert for the insertion tool of FIG. 24.

DESCRIPTION OF THE PREFERRED EMBODIMENT

Referring now to the several drawing figures in which identical elements are numbered identically throughout, a description of the preferred embodiment of the present invention will now be provided.

A. Vertebral Anatomy

Figure 1:
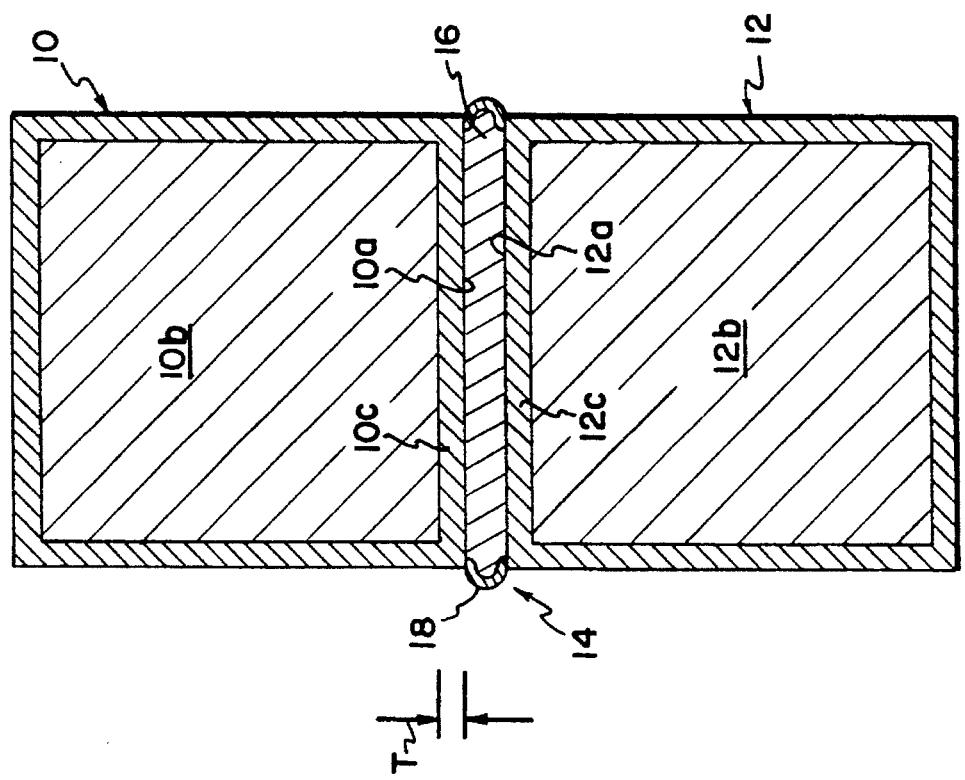
FIG. 1 is a schematic view showing two vertebral bodies separated by a disc material.

With initial reference to FIG. 1, the implant of the present invention is intended for use in facilitating fusion between two vertebrae. FIG. 1 shows, in schematic format, an upper vertebra 10 and a lower vertebra 12. Each of the vertebrae 10,12 are vertically aligned and present opposing end plates 10a,12a. The end plates 10a,12a are separated by a disc 14. The disc 14 includes a fibrous inner material 16. The periphery of the disc 14 is a fibrous material conventionally referred to as the annulus 18. The interior of each of the vertebrae 10,12 consists of soft, cancellous bone 10b,12b. At the end plates 10a,12a, the vertebrae 10,12 include hard cortical bone layers 10c,12c. The cortical bone layers commonly have a thickness T of about 2 mm.

In interbody fusion placement, it is desirable to provide a bore to receive the fusion implant with the bore formed through the disc space 14 between the opposing vertebrae 10,12 and with the bore cutting through the cortical bone 10c,12c of the end plates 10a,12a. As a result, the cancellous bone 10b,12b of each of the vertebrae 10,12 is exposed and opposing the implant. Exposure of the cancellous bone is desirable since such cancellous bone 10b,12b is substantially laden with blood vessels. The cancellous bone is the most rapidly growing and forms the bone growth linking the vertebrae 10,12 upon completion of the spinal fusion therapy.

While exposure of the cancellous bone is desirable for the purpose of facilitating bone growth, the opposition of the implant to the cancellous bone increases the probability of subsidence since the cancellous bone is relatively soft and undesirable for the purposes of weight bearing.

B. Prior Art Implants

Figure 1A:
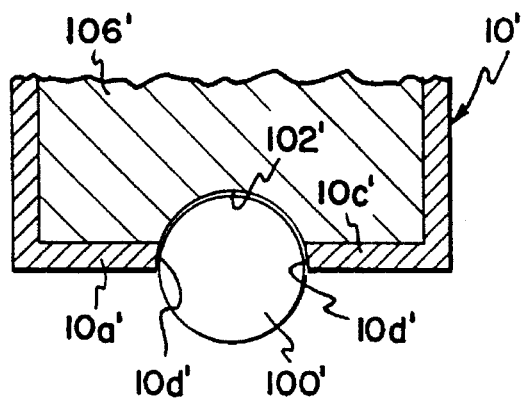
FIG. 1A is an end view of a prior art interbody device opposing a vertebra.
Figure 1B:
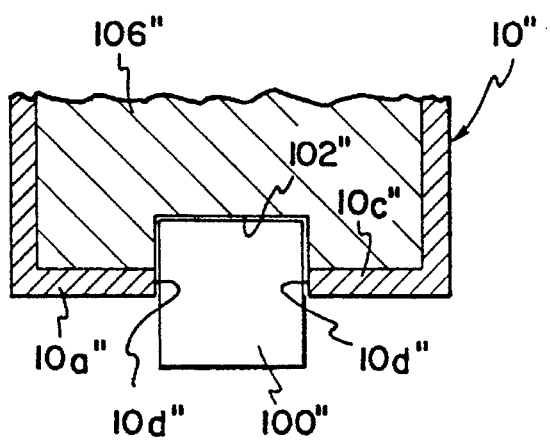
FIG. 1B is an end view of a different prior art intervertebral fusion device opposing a vertebra.
Figure 1C:
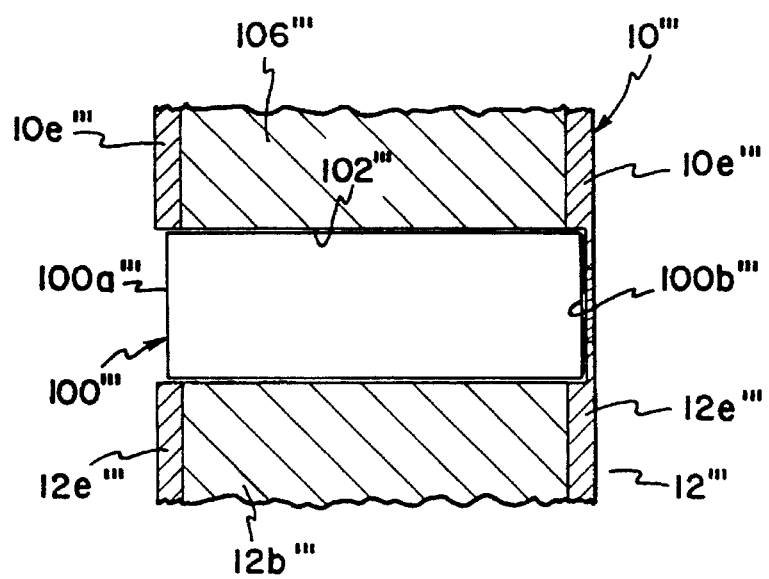
FIG. 1C is a side sectional view of an interbody device received between two vertebrae.
Figure 2:
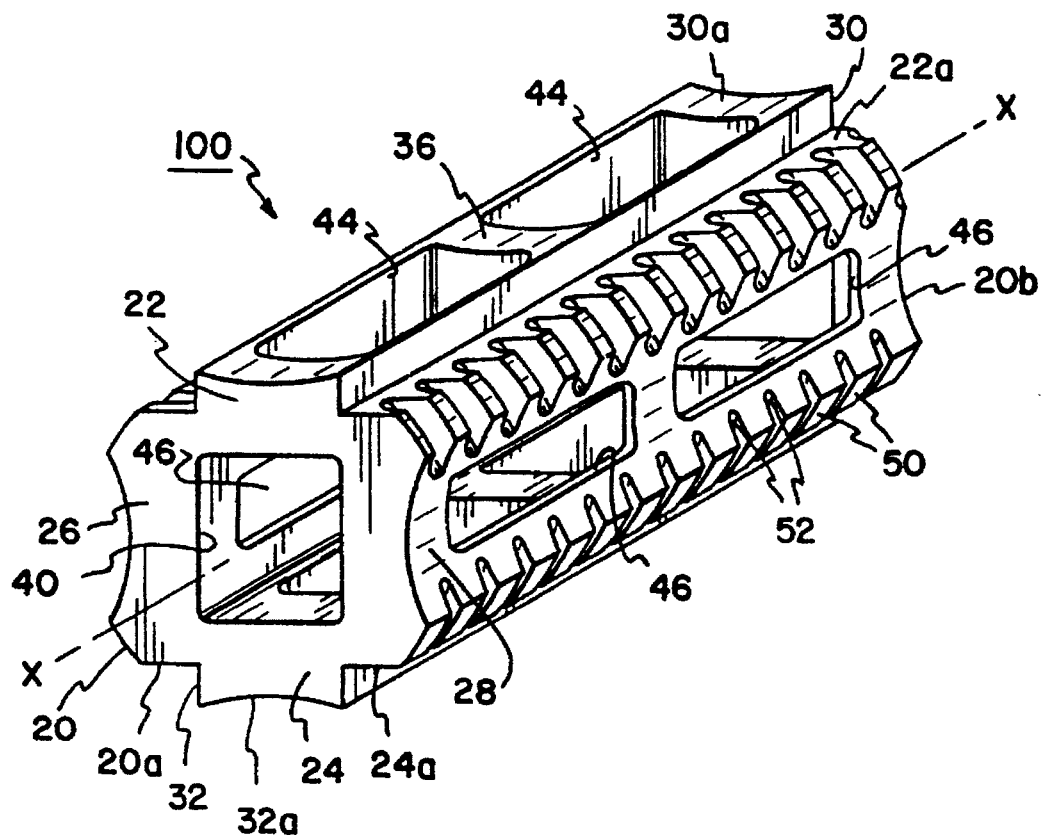
FIG. 2 is a front, right side and top perspective view of an implant according to the present invention.

With the anatomy thus described, disadvantages and problems associated with prior art implants can best be understood with references to FIGS. 1A, 1B and 1C. FIG. 1A shows an implant 100' positioned within a bore 102' formed in an upper vertebrae 10'. For purposes of illustration, a lower vertebrae is not shown in FIG. 1A but it will be appreciated that the lower vertebrae is similarly bored as upper vertebrae 10'. The intervertebral implant 100 shown in FIG. 1A is a generally cylindrical threaded implant such as that shown in U.S. Pat. No. 5,015,247. The bore 102' is an arc of a cylinder size to receive the implant 10'. So formed, the cortical bone 10c' of end plate 10a' is provided with angled surfaces 10d' opposing the implant 100'. The surfaces 10d' are the areas of greatest support since this is where the implant 10' bears against the cortical bone 10c'. Unfortunately, the surfaces 10d are of small surface area when compared to the total surface of the implant 100. Due to the angled surfaces 10d', the implant 100' is susceptible to slippage relative to the end plate 10a'. Upon occurrence of such slippage, subsidence of the implant 100' into the soft cancellous bone 10b' occurs. This subsidence causes the disc space to collapse and revert back to its pre-surgical condition.

FIG. 1B also shows a cross sectional view with an implant 100" such as that shown in U.S. Pat. No. 4,834,757. The implant 100" is substantially rectangular in cross section. The vertebra 10" is provided with a complementarily shaped bore 102". As a result, the cortical bone 10c" of the end plate 10a" opposes the implant 100" at generally vertical surfaces 10d". In this example, the cortical bone 10c" provides no bearing surface opposing migration of the implant 100" into the cancellous bone 10b".

To prevent migration of either cylindrical or rectangular cross section implants into cancellous bone, certain prior art devices size the implant to rest on the vertical cortical bone surfaces of the vertebra. For example, FIG. 1C shows an implant 100''' (which could be either circular or rectangular in cross section), positioned between an upper vertebra 10''' and a lower vertebra 12'''. Each of the vertebrae 10''',12''' have outer vertical walls of cortical bone 10e''',12e'''. A bore 102''' is formed between the opposing vertebra 10''',12'''. The bore has a longitudinal length such that the ends 100a''' and 100b''' of implant 100''' bear directly against and oppose the cortical bone 12e''',10e''' In this method of implantation, the implant 102' completely spans the soft cancellous bone 10b''',12b'''. In viewing FIG. 1C, the reader will note that in the absence of an implant length spanning the vertebra, the implant will subside into soft cancellous bone.

Examples of prior art teachings showing implants being sized and positioned to span soft cancellous bone and bear directly against cortical bone is shown in both U.S. Pat. No. 4,834,757 and U.S. Pat. No. 4,743,256. A disadvantage with the technique of having an implant sized and positioned such that it spans the soft cancellous bone and bears directly upon the outer cortical walls of the vertebra is that the bore forming operation for placement on the implant must be precisely controlled as to the length of the bore. The cortical layer against which the implant bears is very thin (approximately 2 millimeters). If the bore length is too small, the implant will not bear on the cortical bone. If the bore length is too great, the boring tool will pierce through the end of the vertebra. If the former occurs, subsidence is highly probable.

The latter can be extremely dangerous. A boring tool piercing through a vertebra can puncture or sever important anatomical features such as the spinal cord, aorta or the like. If such anatomical features are damaged, severe consequences (including paralysis or death) can follow.

C. Parent Application

The following is a description of the implant as appears in parent application Ser. No. 08/247,857. It will be noted that the implant of the present invention provides full bearing on cortical bone while avoiding the need for a precisely controlled-depth of cut.

With initial reference to FIGS. 2–9, an implant 100 is shown. The implant 100 includes a body 20 which is substantially square in cross section. The body extends along a longitudinal axis X—X.

The body 20 includes two generally flat upper and lower bearing walls 22,24. Bearing walls 22,24 are joined by side walls 26,28. Each of the bearing walls 22,24 present outwardly facing bearing surfaces 22a,24a. Each of the bearing surfaces 22a,24a extend generally parallel to each other and parallel to the longitudinal axis X—X.

Projecting perpendicularly away from the center of each of bearing walls 22,24 are raised ridges 30,32. Each of the ridges 30,32 extend parallel to axis X—X and project outwardly from the body 20. The ridges 30,32 are centrally positioned on the bearing surfaces 22a,24a such that the bearing walls 22,24 are exposed along opposite sides of each of the raised ridges 30,32. The ridges 30,32 terminate at concave faces 30a,32a.

Figure 3:
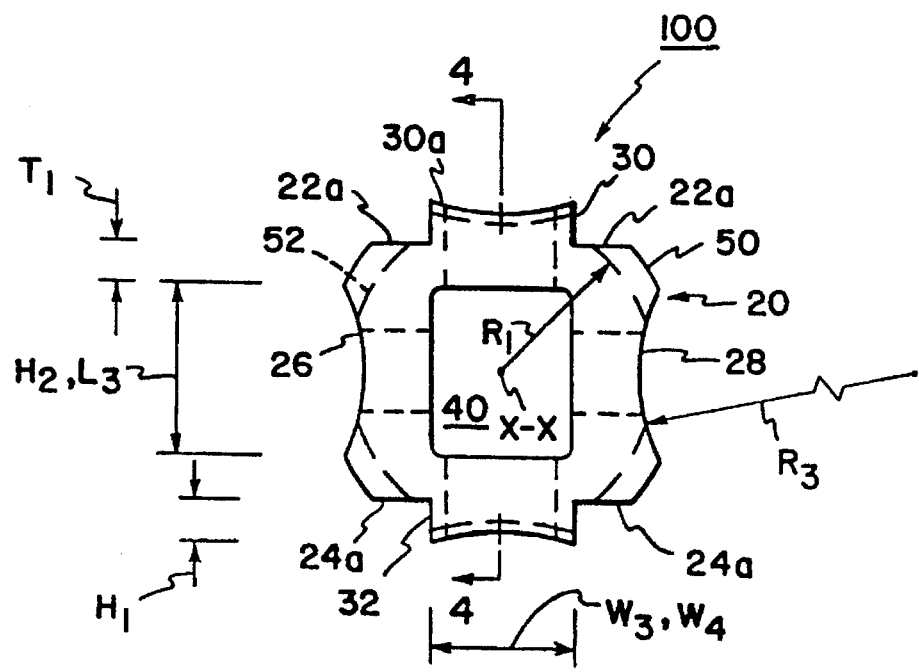
FIG. 3 is an elevation view of a trailing end of the implant of FIG. 2.
Figure 4:
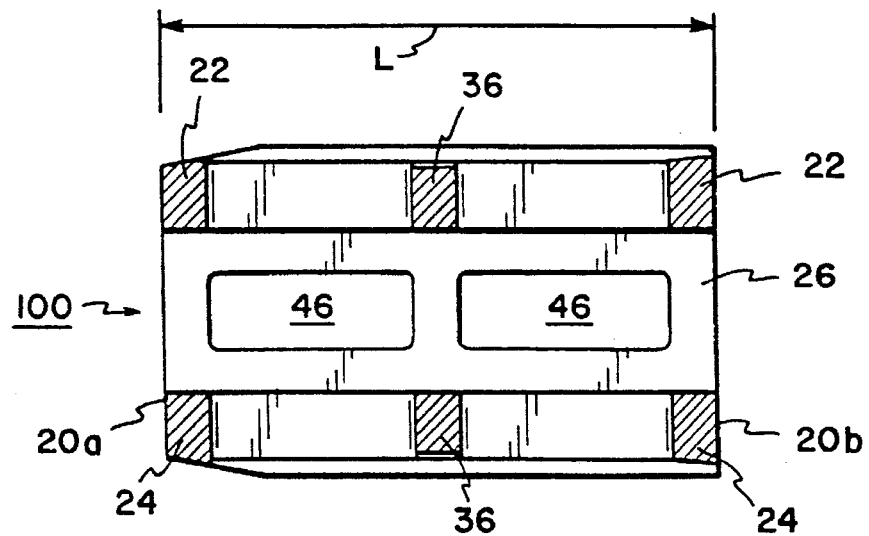
FIG. 4 is a view taken along line 4—4 of FIG. 3.
Figure 5:
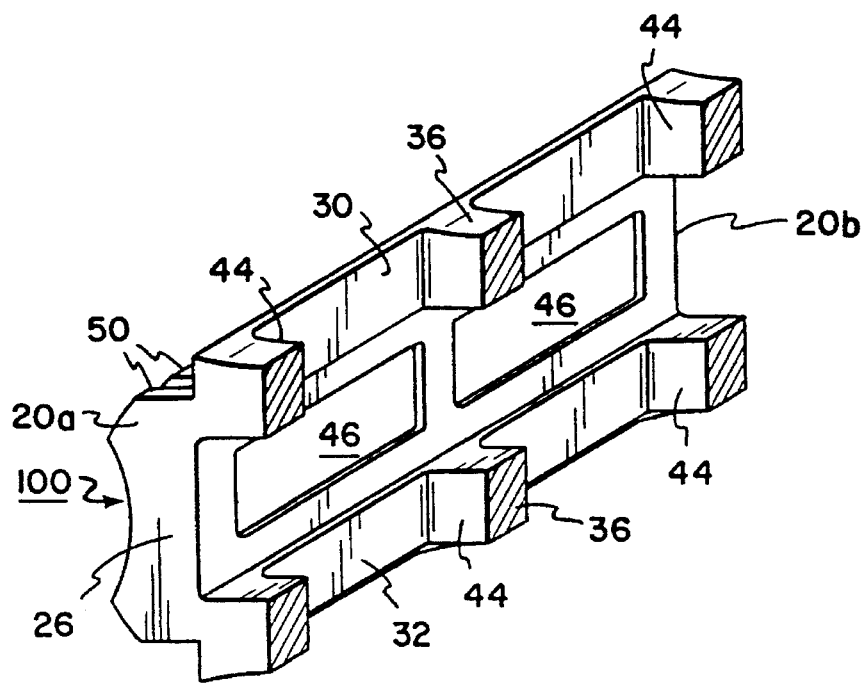
FIG. 5 is a perspective view of the sectioned implant of FIG. 4.
Figure 6:
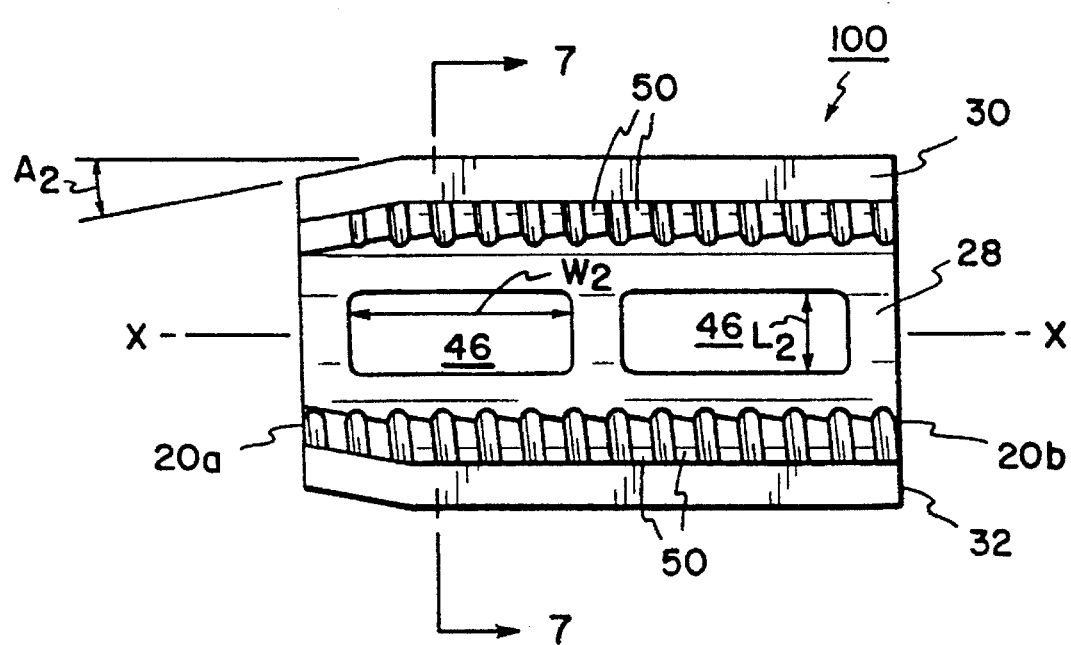
FIG. 6 is a side elevation view of the implant of FIG. 2.
Figure 7:
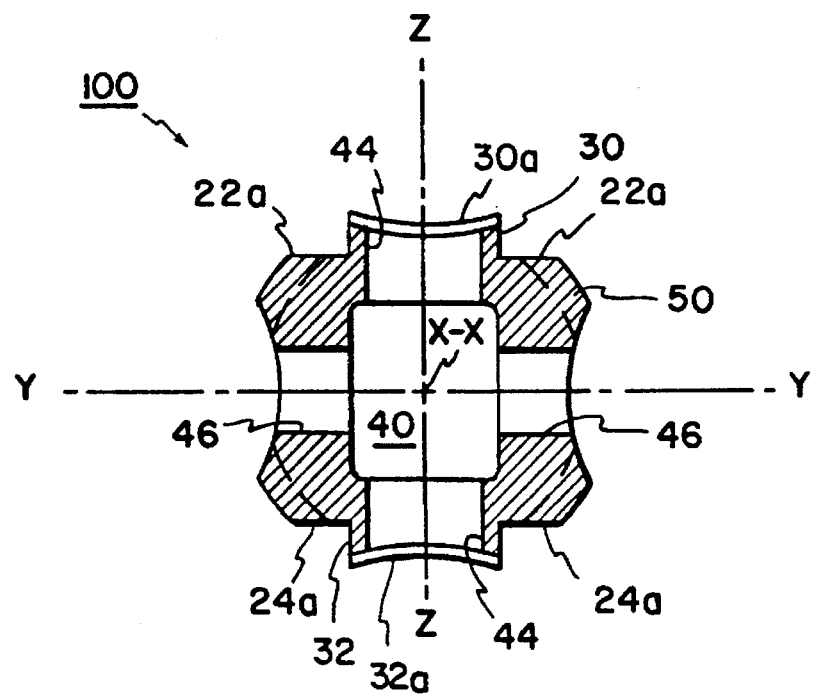
FIG. 7 is a view taken along line 7—7 of FIG. 6.
Figure 8:
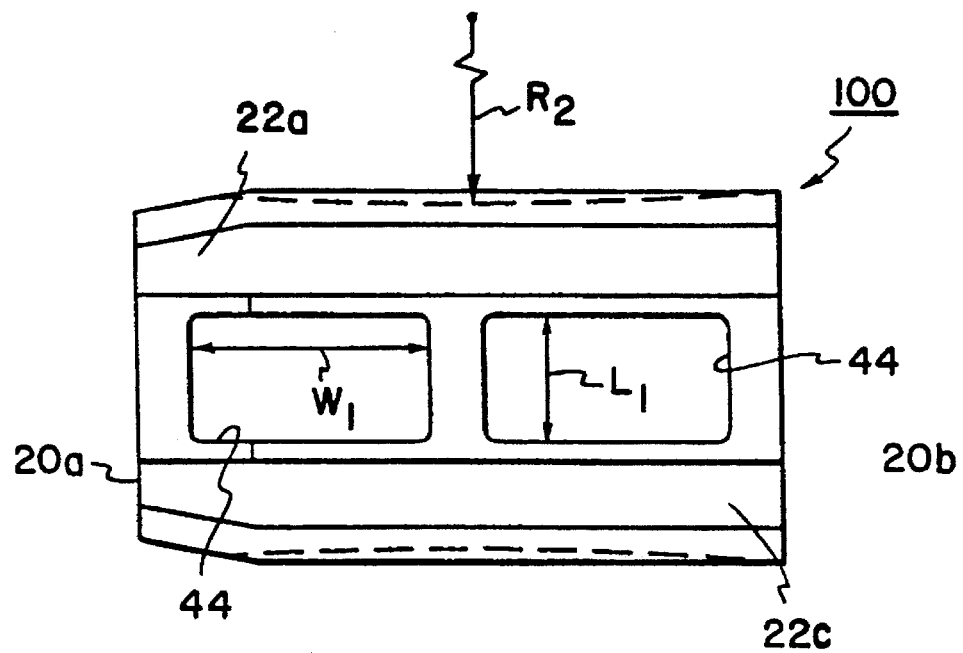
FIG. 8 is a top plan view of the implant of FIG. 2.

The body 20 extends from a leading end 20a to a trailing end 20b. Intermediate ends 20a,20b, side walls 26,28 are joined by reinforcing ribs 36 (see FIGS. 4 and 5):

A bore 40 extends axially through body 20 and extends completely through the leading end 20a and trailing end 20b. Bore 40 is generally rectangular in cross section as best shown in FIGS. 3 and 7.

Formed completely through ridges 30,32 and bearing walls 22,24 are a plurality of openings 44. Openings 44 have an axis Z—Z which is perpendicular to longitudinal axis X—X. Each of the openings 44 is in direct communication with bore 40.

Side walls 26,28 are concave and are provided with openings 46 therethrough in communication with chamber 40. Openings 46 extend along an axis Y—Y which is mutually perpendicular to axes Z—Z and X—X (see FIGS. 6 and 7).

At the edges of intersection between walls 22,24, 26 and 28, a plurality of anchor segments 50 are provided. Between each of the segments 50, a valley, or recess 52 is formed to define the anchor segments 50. The anchor segments 50 are portions of a helix pattern surrounding the axis X—X. Also, as best shown in FIG. 3, the valleys 52 reside on the arc of a circle having radius $R_1$ from axis X—X.

Figure 9:
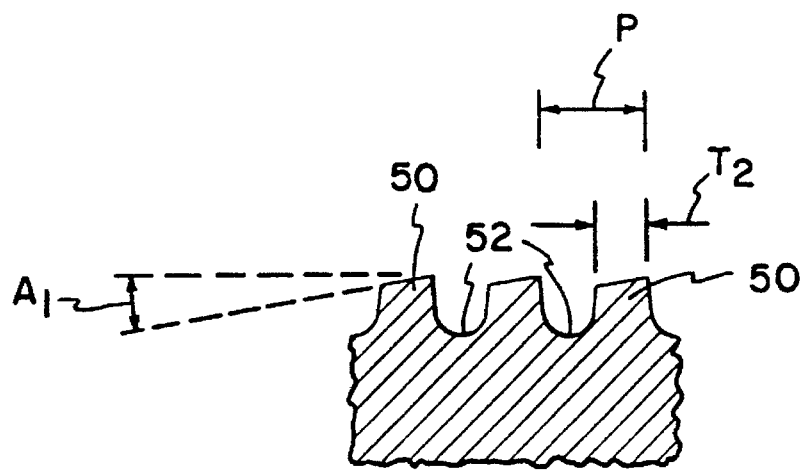
FIG. 9 is an enlarged view of a portion of the anchor detail of FIG. 6.

As shown best in FIG. 9, each of the anchor segments 50 is generally square in cross section with an end of the anchor 50 having an angled surface set at an angle $A_1$ relative to a line parallel to the axis X—X and slanted downwardly towards the leading end 20a. In a preferred embodiment, angle $A_1$ is 10 degrees.

In a preferred embodiment, the cross sectional area of the implant is not uniform throughout its longitudinal dimension. With best reference to FIGS. 3 and 8, the outer faces 30a,32a of the ridges 30,32 and the side walls 26,28 are radiused inwardly as indicated at radii $R_2,R_3$. The benefits of the radii $R_2,R_3$ will be more fully described. $R_3$ equals the outside diameter of anchors 50. Further, the leading end 20a is provided with a taper angle $A_2$ (FIG. 6) which, in a preferred embodiment, is 10 degrees.

As will be more fully described, the implant 100 is placed within a bore formed between two vertebra. The formation of the bore relative to the sizing of the implant is important for reasons that will become apparent. Accordingly, for the purposes of illustrating a preferred embodiment, the presently anticipated dimensions of the implants 100 will be given. It will be appreciated that various sizes of implant 100 will be available to accommodate different sized patients and different regions in the spine.

1. Length of implant L (FIG. 4): 28 millimeters;
2. Size of bores 44 ($L_1 \times W_1$, see FIG. 8): 0.416 inches by 0.216 inches;
3. Size of bores 46 ($L_2 \times W_2$, see FIG. 6): 0.416 inches by 0.150 inches;
4. Radius $R_1$ (FIG. 3) from axis X—X to valleys 52: 7.5 millimeters;
5. Size of cross section of bore 40 ($W_3 \times L_3$): 7 millimeters by 8 millimeters;
6. Width ($W_4$, see FIG. 3) of ridges 30,32: 7 millimeters;
7. Height ($H_1$, see FIG. 3) of ridges 30,32: 1 millimeter;
8. Height ($H_2$, FIG. 3) of convex area of side walls 26,28: 8 millimeters;
9. Thickness ($T_1$, FIG. 3) of bearing walls 26,28: 2 millimeters;
10. Pitch (P, FIG. 9) of anchors 50: 2.3 mm;
11. Thickness ($T_2$, FIG. 9) of anchors 50: 1 mm.
12. Radius $R_2$ (FIG. 8): 190 mm; and
13. Radius $R_3$ (FIG. 3): 8.75 mm.

Figure 10:
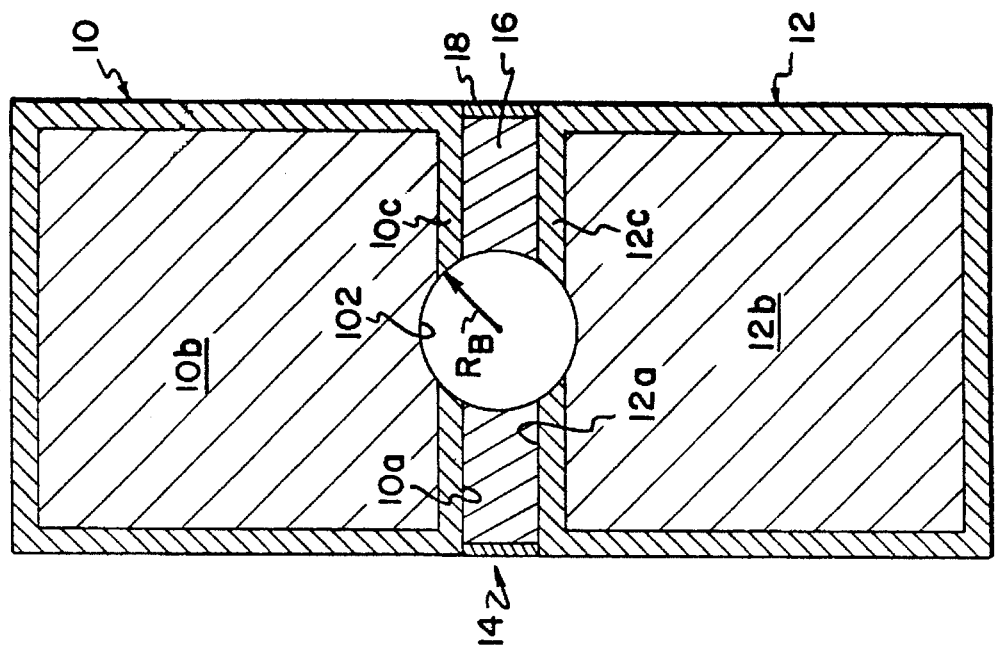
FIG. 10 is an end view of two vertebrae formed with a bore there between and stretched apart to receive the implant of FIG. 2.

To place the implant 100 between the vertebra 10,12 attention is now directed to FIG. 10. The vertebra 10,12 are distracted to stretch the annulus 18. A bore 102 is formed with its cylindrical axis extending parallel to and centrally positioned between the end plates 10a,12a. The bore 102 is sized for its radius $R_B$ to be equal to the radius ($R_1$) of the implant 100 (as shown in FIG. 3) to the valleys 52. The implant 100 and bore 102 are sized such that the radius $R_B$ will extend through the cortical layers 10c,12c without extensive penetration into the soft cancellous bone 10b,12b.

For the reasons that will become apparent, bore 102 must be precisely sized and accurately positioned with the axis of the bore 102 centrally positioned between the end plates 10a,12a and parallel to the end plates 10a,12a. A surgical method and kit for accomplishing such an accurate formation of a bore between vertebra is the subject of commonly assigned and co-pending U.S. patent application Ser. No. 08/015,863, filed Feb. 10, 1993 (also shown in International Publication No. WO 94/17759 dated Aug. 18, 1994, on PCT Application No. PCT/US94/00586).

Figure 13:
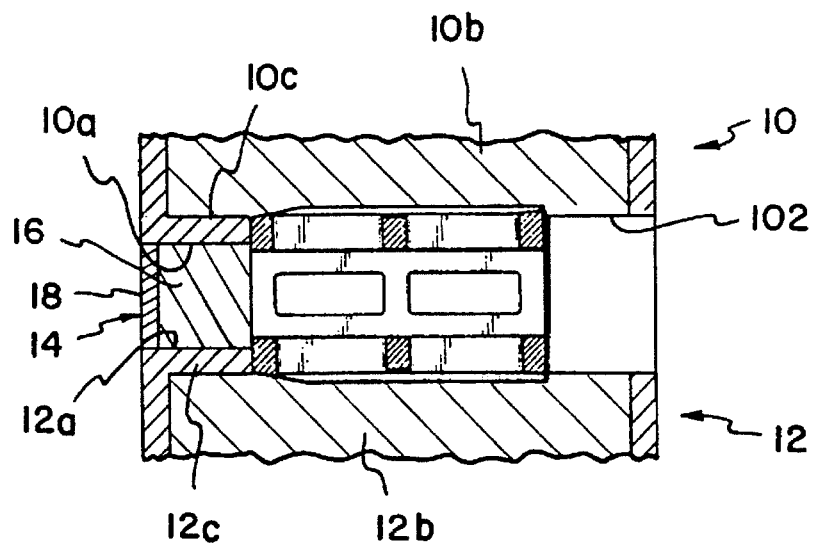
FIG. 13 is a side sectional view of an implant shown inserted between two vertebrae.

With bore 102 thus formed, the implant 100 is inserted into the bore 102 with the leading end 20a first introduced into the bore 102. The implant 100 is rotated about its axis X—X to advance the implant 100 into the bore 102 to the position shown in FIG. 13. Alternatively, implant 100 need not be rotated but simply can be impacted by driving it axially along its axis X—X. The implant 100 is positioned such that upon full insertion into the bore 102, openings 44 are directed toward the soft cancellous bone 10b,12b. The openings 46 are directed toward the space formerly occupied by removed disc material 16.

Figure 11:
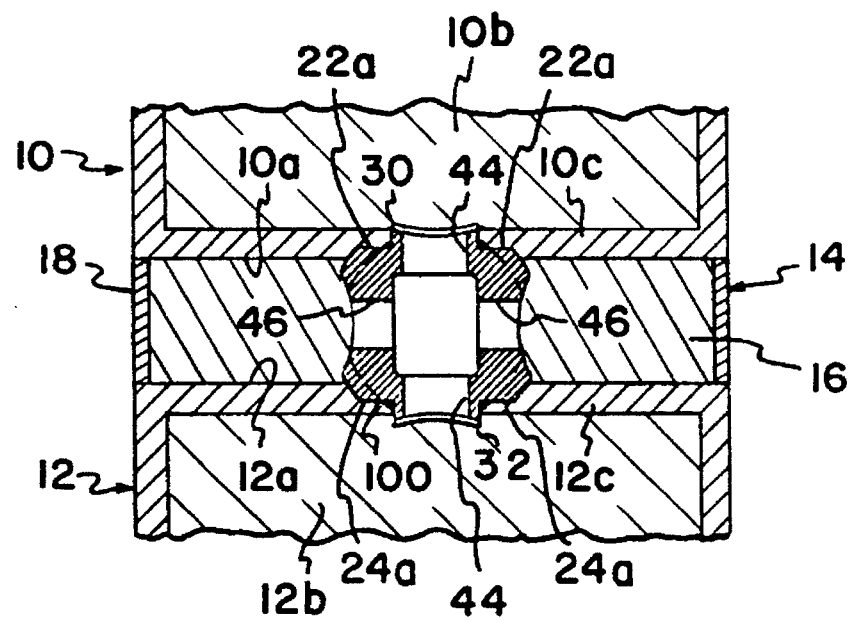
FIG. 11 is the view of FIG. 10 showing the implant of FIG. 2 inserted within the bore of FIG. 10.

With the radius $R_B$ of the bore selected to equal the radius $R_1$ to the valleys 52, after insertion of the implant, the bearing surfaces 22a,24a directly oppose and abut the cortical layer 10c,12c of the end plates 10a,12a(see FIG. 11). Also, with the relative sizing of the bore 102 thus described, the ridges 30,32 protrude beyond the cortical bone layer 10c,12c into the soft cancellous bone 10b,12b. With this structure and positioning of the implant 100, a surgeon can place bone chips within the bore 40. Accordingly, the bone 10b,12b is fused together by a bone column formed through the aligned bores 44,40. The load bearing of the surfaces 22a,24a against the cortical bone 10c,12c prevents subsidence of the implant 100 into the cancellous bone 10b,12b. The bearing surfaces 22a,24a are parallel to the implant 100 as opposed to current devices where a rounded surface contacts the implant 100 at an angle (e.g., U.S. Pat. No. 5,015,247) or rectangular devices where there is no end plate contact except at the extreme ends of the implant (e.g., U.S. Pat. No. 4,834,757). Also, the present implant 100 has non-threaded ridges 30,32 that project through the end plate 10a 12a and directly contact the cancellous bone 10b,12b. The surface area of the bores 44 is made as large as possible while permitting structural integrity to the implant 100 to provide maximum porosity to cancellous bone growing through the implant 100.

Figure 12:
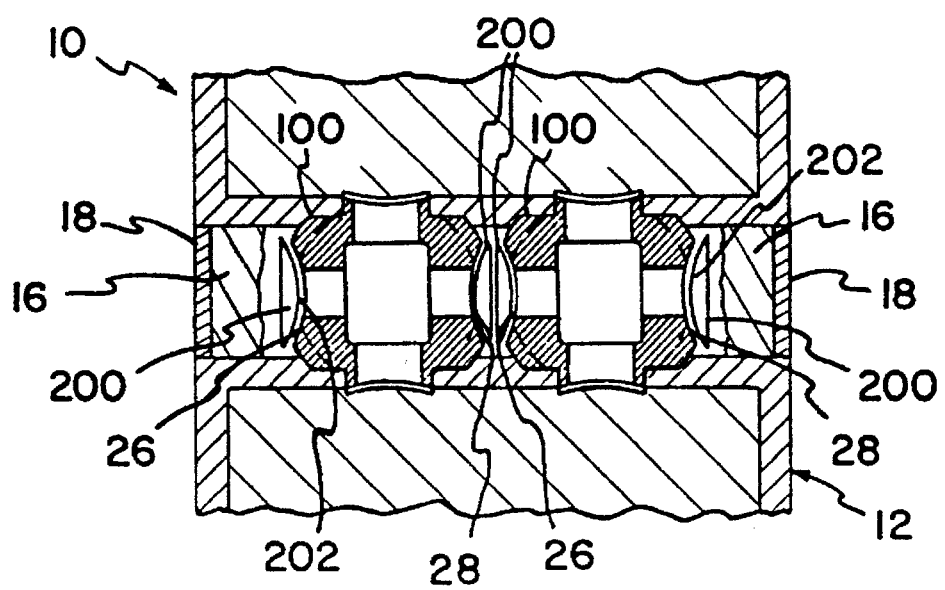
FIG. 12 is a view similar to that of FIG. 11 showing two implants disposed between opposing vertebrae.

In FIG. 11, a single implant 100 is shown inserted. In many applications (particularly in the lumbar region of the spine), two implants disposed in parallel alignment are preferred. Such a positioning is shown in FIG. 12. Also, in FIG. 12, it will be noted that the implants 100 are in close proximity. The closeness of proximity is attained by the concave side walls 26,28.

Normally, with convex side walls such as that shown in U.S. Pat. No. 5,015,247, implants cannot be placed with their axes in close proximity. Also, with threaded convex side walls, the implants of U.S. Pat. No. 5,015,247 cannot be allowed to touch. If the second implant to be inserted touches the first previously inserted implant, the second implant can cause the first implant to unscrew as the second implant is advanced. This creates a potentially dangerous situation where the previously inserted implant can be inadvertently unthreaded into a major vessel or the spinal cord. As a result in certain regions of the spine, only one implant can be placed while two would otherwise be desirable.

With the concave side walls 26,28, the present implants can be placed in closer proximity increasing the likelihood that two implants can be used at any disc level.

In the embodiment of FIG. 12, bone dowels 200 are positioned between both implants 100 and opposing the side walls 26,28 of the implants 100 on both sides thereof. The dowels have convex arcuate outer surfaces 202 shaped to conform with the concave surfaces of the side walls 26,28. Bone dowels 200 are placed on the exterior side walls such that all bores 46 are in direct opposition to a bone dowel 200. With this application, disc material 16 is blocked by the bone dowels 200 from entering into the interior of the implants 100 and interfering with bone growth through the implants 100. Further, the bone growth through the bores 44,40 fuses with the bone growth through the side bores 46 and fuses with the bone dowels 200. Accordingly, the linkage between the vertebra 10,12 is enhanced since each of the implants 100 is cross linked.

Figure 14:
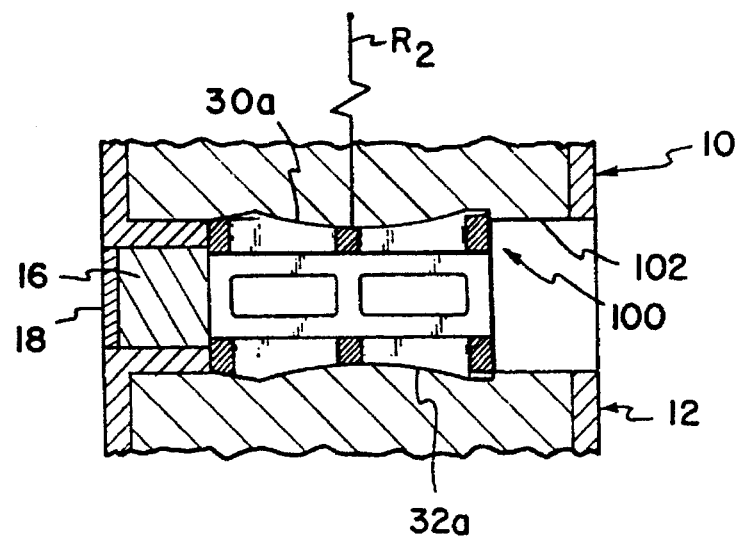
FIG. 14 is a schematic representation of the view of FIG. 13 showing radiused surfaces of the implant in great exaggeration for purpose of illustration.
Figure 17:
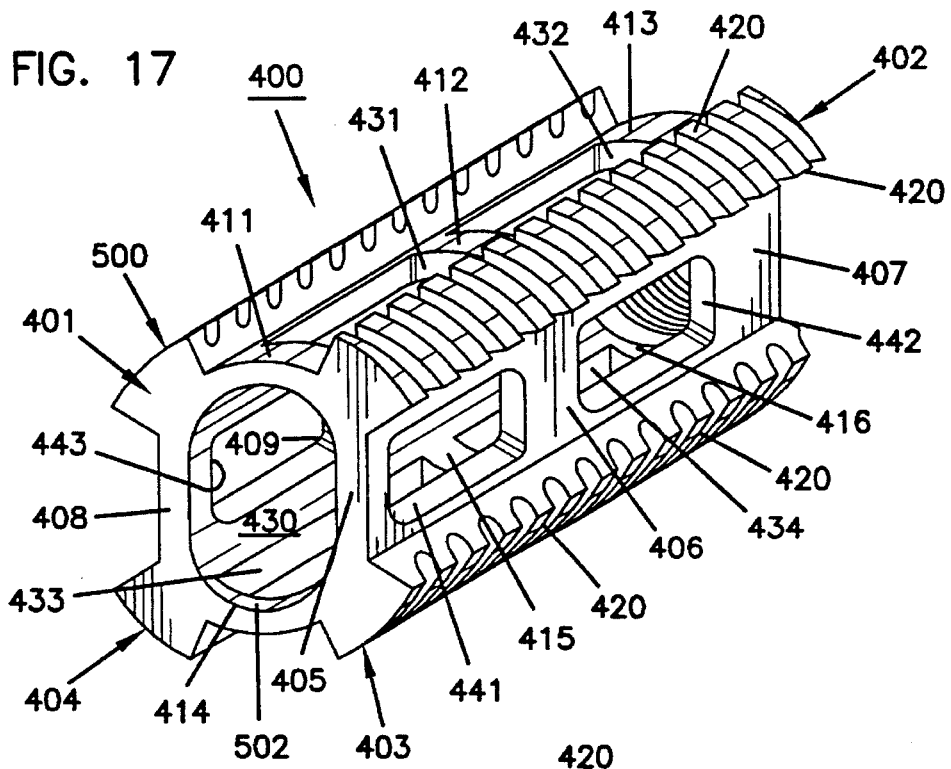
FIG. 17 is a perspective view of a still alternative embodiment of the present invention.
Figure 18:
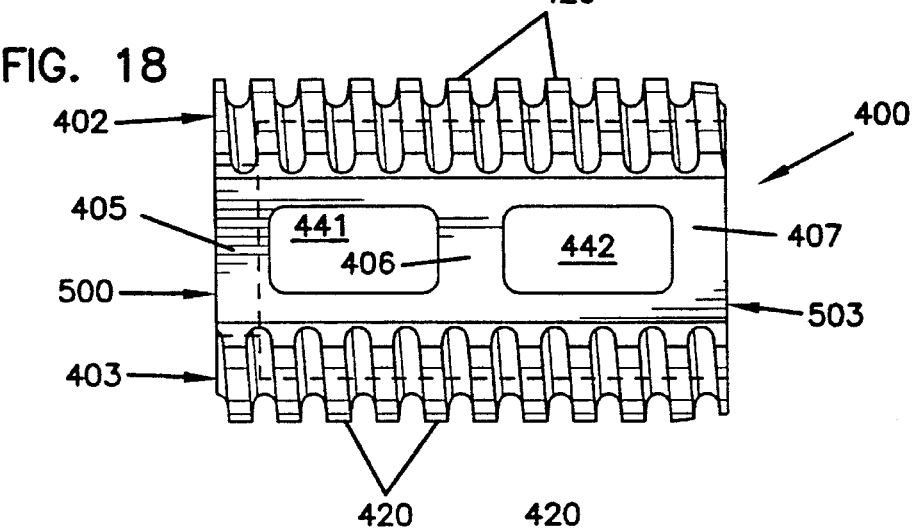
FIG. 18 is a side elevation view of the implant of FIG. 17.
Figure 19:
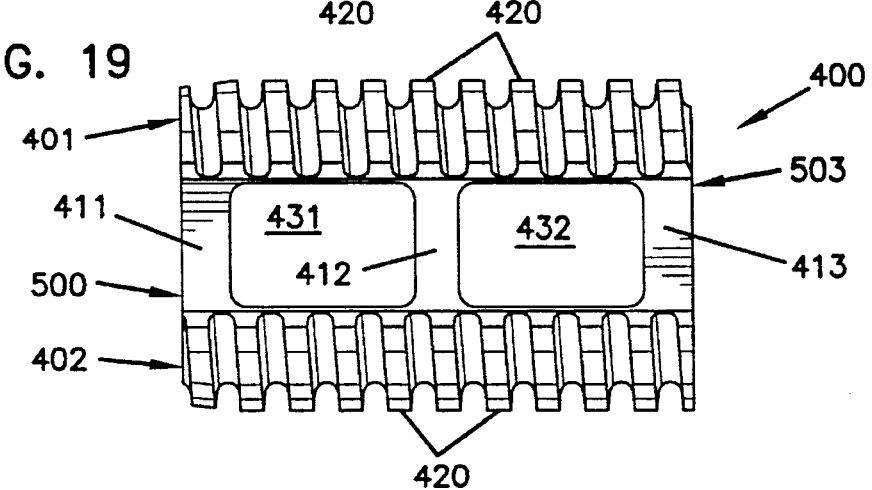
FIG. 19 is a top plan view of the implant of FIG. 17.
Figure 20:
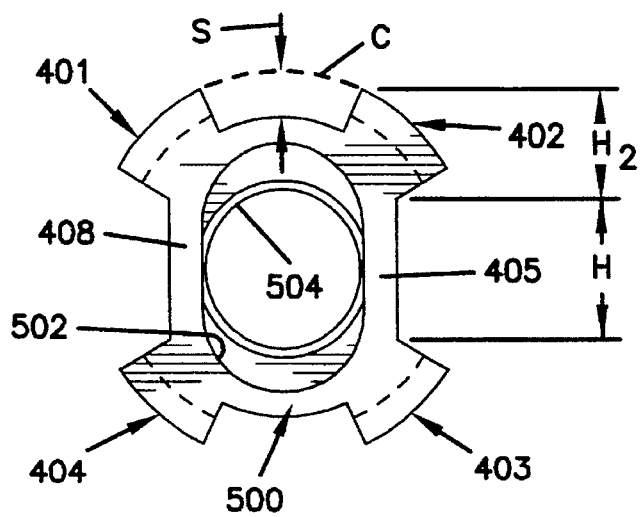
FIG. 20 is a leading end view of the implant of FIG. 17.
Figure 21:
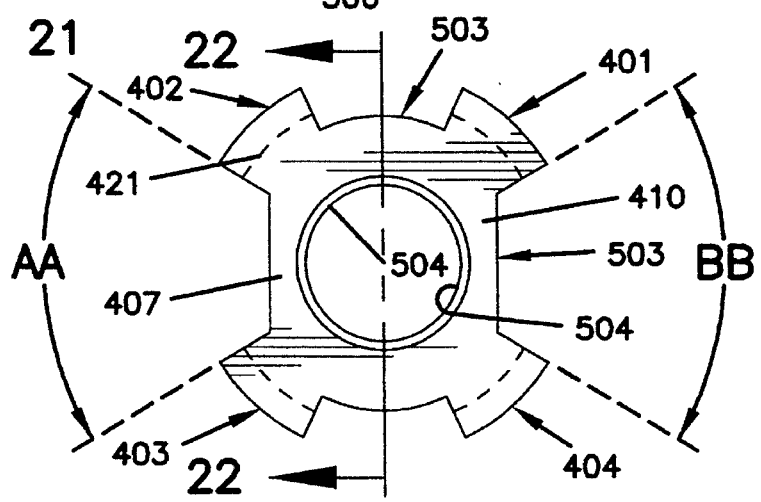
FIG. 21 is a trailing end view of the implant of FIG. 17.
Figure 22:
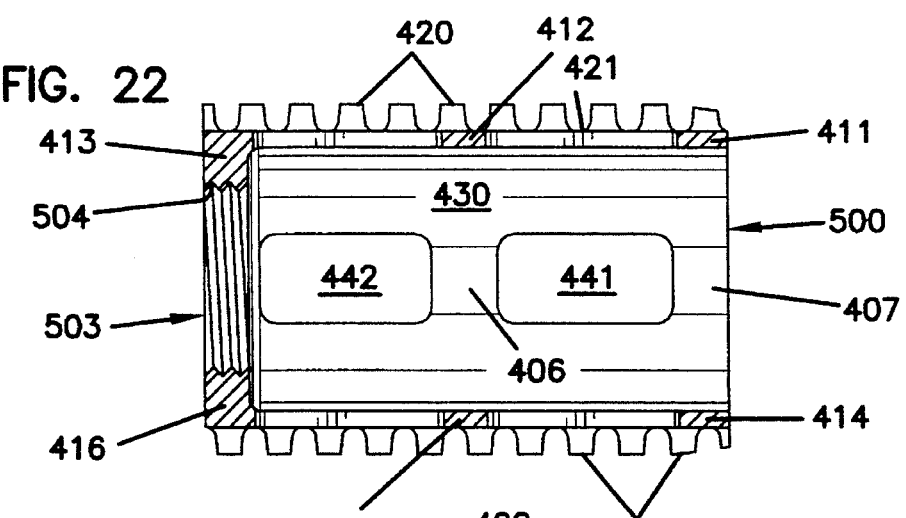
FIG. 22 is a view taken along line 22—22 of FIG. 21.
Figure 23:
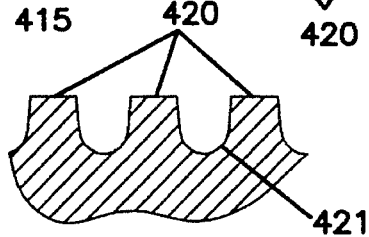
FIG. 23 is an enlarged sectional view of a thread pattern of the implant of FIG. 17.
Figures 24, 25:
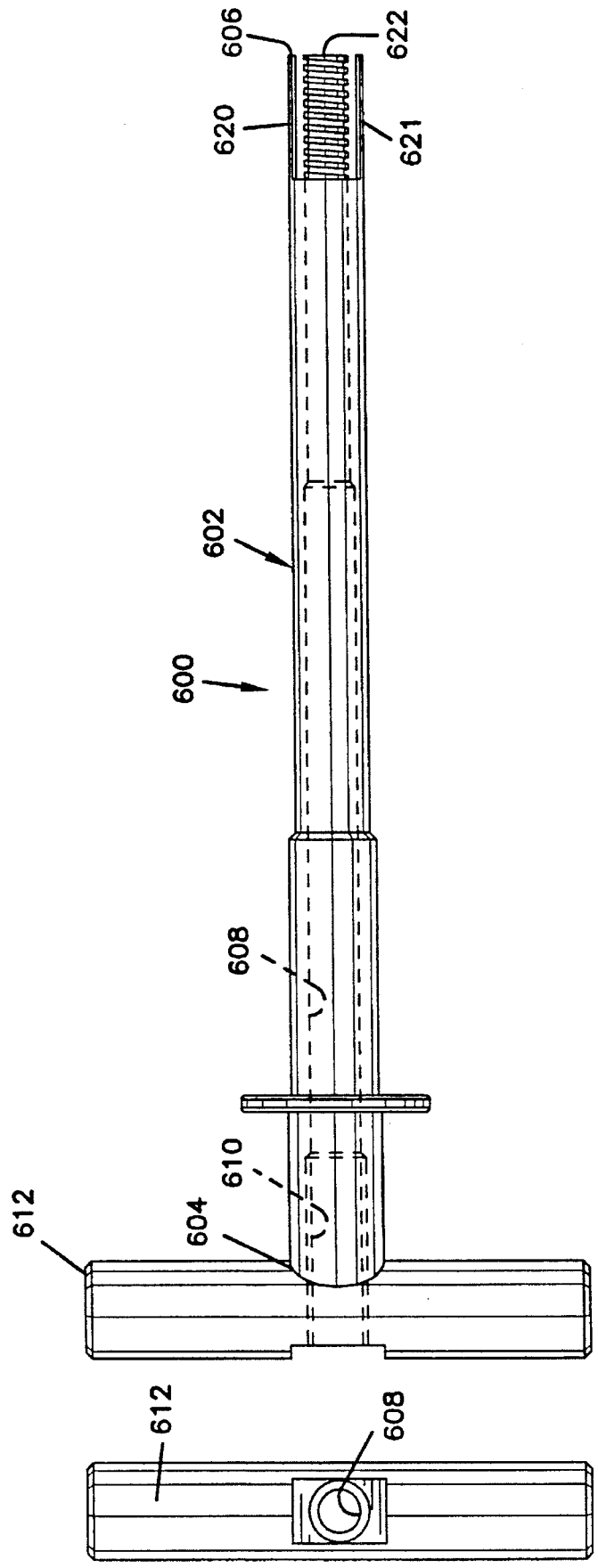
FIG. 24 is a side elevation view of an insertion tool for use with the implant of FIG. 17.
FIG. 25 is a proximal end view of the insertion tool of FIG. 24.

FIG. 14 illustrates the value of the non-uniform cross-section of implant 100. Namely, the dip $R_2$ (shown exaggerated in FIG. 14 for purpose of illustration) in both of the walls 30a,32a and the side walls 26,28 prevents movement of the implant 100 along its axis X—X after the bone growth is achieved.

Figure 15:
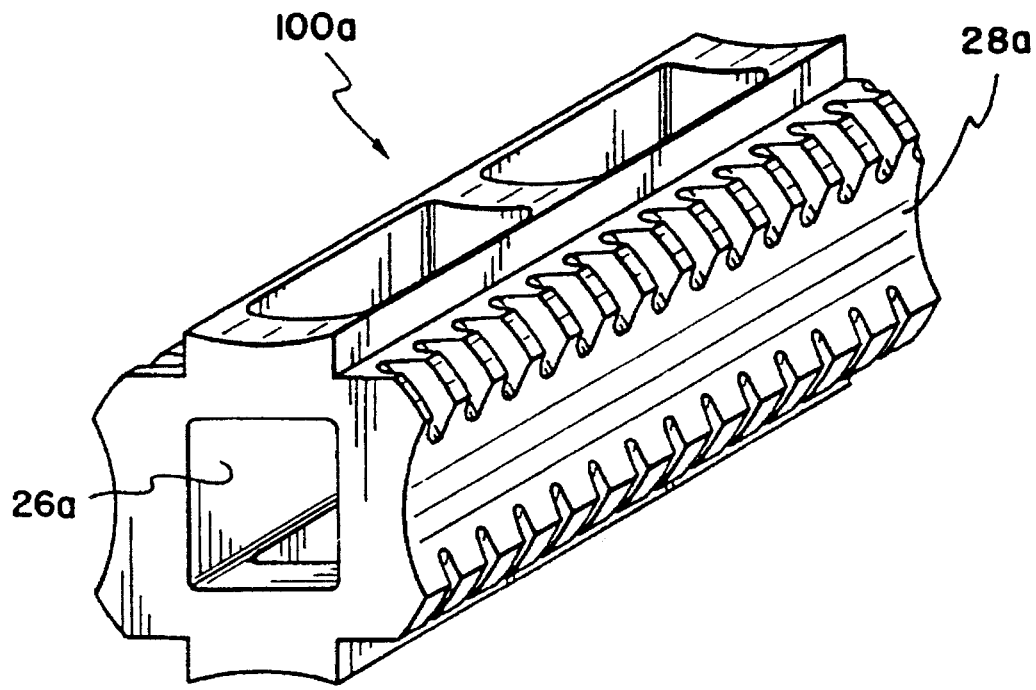
FIG. 15 is a perspective view of an implant alternative embodiment.

In the event a surgeon prefers not to use bone dowels 200 in the manner indicated in FIG. 12, it is desirable not to have the side wall openings 46 opposing disc material in order to prevent such disc material from entering into the implant 100 and interfering with bone growth through the implant 100. Accordingly, FIG. 15 shows an alternative embodiment implant 100a where the side walls 28a,26a are solid and do not include openings 46. Accordingly, there is no direct communication between the disc material and the interior of the implant 100a.

Figure 16:
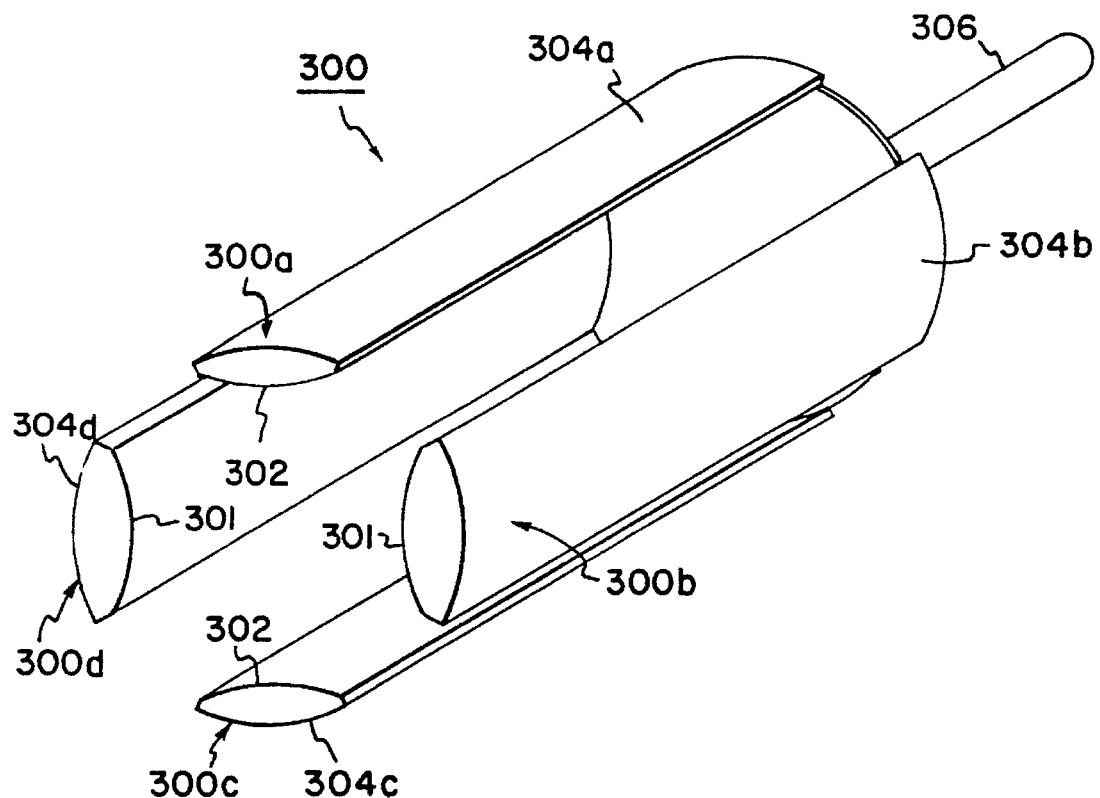
FIG. 16 is a view of a tool for placement of the implant within a bore.

FIG. 16 shows an insertion tool 300 for inserting the implant 100. The insertion tool 300 includes four prongs 300a–300d. The prongs 300a–300d cover the openings 44,46 with the thicker prongs 300d,300b having convex inner surfaces 301 sized to complementary mate with the concave side walls 26,28. Further, the thinner prongs 300a, 300c have convex surfaces 302 sized to mate with the concave surfaces 30a,32a of the ridges 30,32. The insertion device 300 covers the holes 44,46 during insertion of the implant 100 to prevent disc material and other debris from entering the interior 40 of the implant 100. Also, the outer surfaces 304a–304d of each of the prongs is generally the arc of a cylinder such that the device 100 within the insertion tool 300 presents a cylindrical surface permitting the non-cylindrical implant 100 to be implanted into a round bore 102. A handle 306 connects the prongs and permits turning or axial driving of the tool 300.

As indicated, it is desirable that bores 44 be of maximum surface area as possible to increase the surface porosity of the implant 100. Applicants, through animal studies and human clinical experience, have found that the larger the surface porosity the greater the probability for successful bone ingrowth into the implant 100.

The invention utilizes the anchors 50 embedded within the end plates 10a,12a to hold the implant 100 in position. Since the end plates 10a,12a are formed of cortical bone 10a,12a, the embedded anchors 50 within the end plates 10a,12a provide substantial force against inadvertent movement of the implant 100. Also, the anchors 50 permit either threading the implant 100 by rotating it about its axis X—X or by implanting while driving the implant 100 and tool 300 with a hammer or the like along its axis X—X. The square cross section anchor 50 is tapered (at $A_1$) to provide resistance to expulsion.

D. Improved Embodiment

With reference now to FIGS. 17–23, an improved alternate embodiment is shown in the form of an implant 400. The implant 400 includes four generally linear thread segments 401,402,403 and 404. A plurality of rigid supports (to be more fully described) retain the thread segments 401-404 in spaced-apart alignment such that the segments 401,404 define the longitudinal edges of a parallelepiped. For ease of explanation, segment 401 will be referred to as a first upper segment, segment 402 is a second upper segment, segment 404 is a first lower segment and segment 403 is a second lower segment.

Segments 402 and 403 are joined by a plurality of rigid supports 405–407 with the supports extending perpendicular to the segments 402,403. Segments 401,404 are similarly joined by rigid supports 408–410 (only supports 408 and 409 being shown in FIG. 17 and support 410 shown in FIG. 21) and being identical to segments 405–407.

The segments 401,402 are joined by rigid supports 411, 412 and 413. Similarly, segments 404,403 are joined by lower convex rigid supports 414,415 and 416.

The threaded segments 401–404 include a plurality of individual threads 420 separated by valleys 421. The individual threads define a completed thread pattern.

In a preferred embodiment, the implant is to be inserted into a threaded bore formed according to the bore forming technique described in the aforementioned and commonly assigned U.S. patent Ser. No. 08/015,863. The thread patterns of the thread segments 401–404 is selected to mate with a threading formed in the bore into which the implant is to be received.

The implant 400 has a hollow interior 430. Opposing surfaces of the segments 401,402 and the upper convex rigid supports 411–413 define two enlarged openings 431,432 which communicate with the interior 430. Similarly, the thread segments 403,404 and lower convex rigid supports 414,415,416 defined two enlarged openings 433,434 which also communicate with the interior 430 and which are vertically aligned with the openings 431,432. Similarly, side openings 441,442,443 and 444 are provided and defined by opposing surfaces of the supports 405–407. The side openings also communicate with the interior 430 and, as will be discussed, upon insertion of the implant oppose the disc space between the vertebrae. Side openings such as 441,442 are optional and the size may be completely closed.

The leading end 500 of the implant is provided with an oval shaped opening 502. The trailing end 503 of the implant is provided with a threaded opening 504.

With the structure thus described, the implant has an improved design such that the threaded segments 401–404 are sized to be received within the cortical bone layer only. The openings 431,432,433 and 434 oppose the cancellous bone of the vertebrae such that bone from the vertebrae grows into the implant 400. Before insertion, the interior 430 is loaded with bone slurry or other bone growth substance by packing the material through opening 502. Additionally, after the implant is inserted, additional bone slurry may be passed through opening 504 in the trailing end 503.

The present design has high structural integrity with the vertical supports 405–410 comprising structural beams, which, after insertion of the implant are parallel to the collapsing forces causing the vertebrae to otherwise move together. Accordingly, the geometry of the vertical supports 405–410 provides the maximum strength for opposing collapsing forces acting on the implant 400. The present design also permits two implants to be placed in the same disc space in close tolerance. Preferably, the implant is selected such that during use, the distance, H, (FIG. 20) between upper and lower thread segments (e.g. between segments 402,403 and 401,404 is selected to equal the desired distracted disc space into which the implant 400 is to be inserted. The remaining height $H_2$ (FIG. 20) is selected to equal the thickness of the cortical bone.

The present invention utilizes a novel insertion tool for placement. The insertion tool 600 is shown in FIGS. 24–29.

The insertion tool 600 includes a tool body 602 extending from a proximal end 604 to a distal end 606. An internal bore 608 extends completely through the tool from the proximal end 604 to the distal end 606.

At the proximal end 604, the bore 608 is provided with internal threads 610. A handle 612 is provided at the proximal end 604 to permit a surgeon to manipulate the tool 600.

Figure 26:
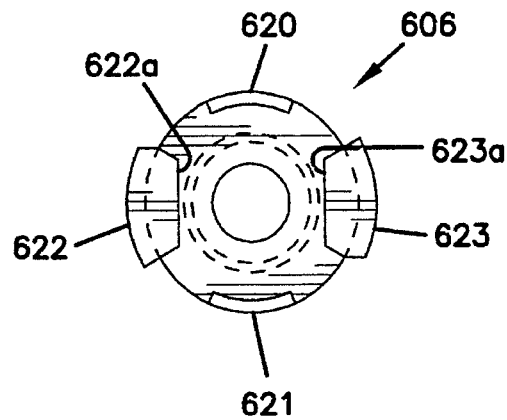
FIG. 26 is a distal end view of the implant of FIG. 24.
Figure 27:
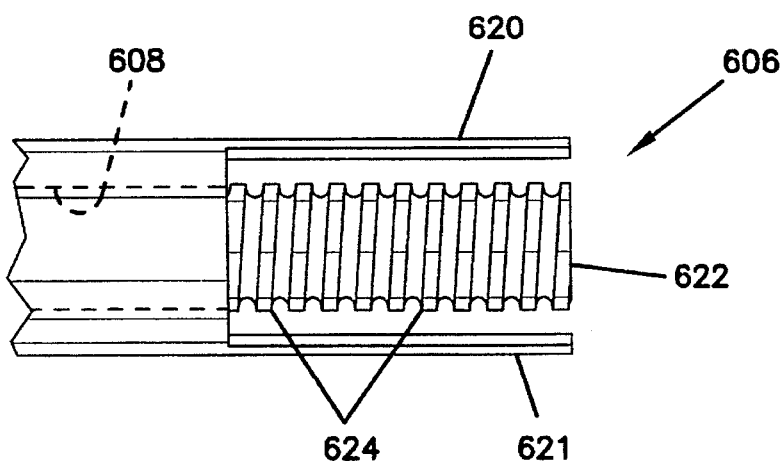
FIG. 27 is an enlarged side elevation view of the distal end of the insertion tool of FIG. 24.
Figure 28:
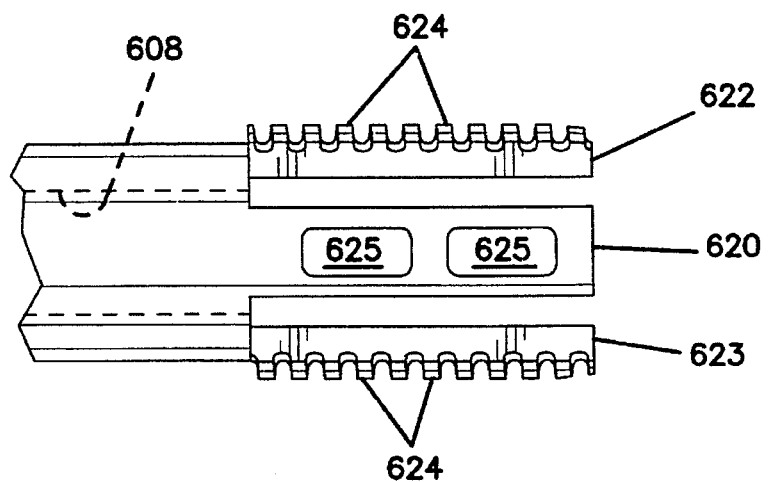
FIG. 28 is the view of FIG. 27 rotated 90 degrees.
Figure 29:
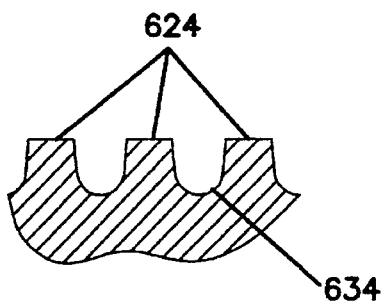
FIG. 29 is an enlarged sectional view of a portion of the thread pattern of the insertion tool distal end.

At the distal end 606, a plurality of grips are provided as best shown in FIGS. 26–28. The grips include unthreaded grips 620,621 and threaded grips 622,623. Grips 620,621 are arcuate with their opposing surfaces selected to complimentary mate with the arc of the convex support ribs 411–416 of implant 400. The thickness of the grips 620,621 is selected for the grips not to extend beyond the, S, (FIG. 20) defined by the arcuate support ribs and an imaginary circle, C, drawn between the threaded segments. Accordingly, upon insertion of an implant 400 into the distal end 606 (as will be described), the grips 620,621 do not protrude beyond the external dimensions of the implant 400.

The threaded grips 622,623 have flat interior surfaces 622a,623a sized to abut the flat external surfaces of the side support ribs 405–410 of the implant 400. The exterior surfaces of the grips 622,623 are provided with threads 624 and valleys 634 having the same thread pattern as the thread segments 401–404 of the implant 400. The unthreaded grips 620,621 are also, in a preferred embodiment, provided with openings 625 (FIG. 8) sized and positioned to align with the openings 431,432 when the implant 400 is placed within the distal end 606 as will be described. Alternatively, openings 625 may be omitted.

With reference now to FIGS. 30, 31, an implant 400 is shown received within the distal end 606. As shown, the thread pattern 624 of the threaded finger 622,623 matches the thread pattern 420 of the threaded segments 401–404 of the implant 400 to define a generally continuous thread pattern through the combination of the implant 400 and the tool 600. Furthermore, holes 431,432,433,434 are in alignment with holes 625, such that bone slurry or the like can freely pass through the openings during the insertion of the tool 600 and the implant 400 into the bore. Also, as shown in FIG. 31, the unthreaded grips 620,621 of tool 600 do not extend beyond the valleys 421 of the thread segments 401–404.

In the embodiment shown, the implant 400 is symmetrical about its longitudinal axis. For example, with reference to FIG. 21, an angle AA from the longitudinal axes to thread segments 402,403 equals a similarly measured angle BB between thread segments 401,404. To fit on tool 600, grips 620,621 are sized to fit between segments 402,403 and 401,404. To prevent inadvertent backwards placement of implant 400 in tool 600, the implant could be non-symmetrical (i.e., with angles AA and BB being unequal). The grips 620,621 would then be complementarily sized. Accordingly, the grips 620,621 would only fit around the implant 400 if the positioning of the implant 400 is proper (i.e., if trailing end 503 is adjacent tool 600).

With the implant 400 retained within the insertion tool 600 as shown in FIGS. 30,31, the insertion tool 600 is used to threadedly place the implant 400 in the prepared threaded bore between the vertebrae. Surgeons simply rotate handle 612 to advance the combination of the insertion tool distal end 606 and the implant 400 into the threaded bore. The turning of the tool handle 612 continues until the implant 400 is placed at a fully inserted position and with holes 431,432,433,434 opposing the cancellous bone of the opposing vertebrae. So installed, the unthreaded grips 620,621 face the bone of the vertebrae. Since these fingers 620,621 are not threaded, they can be easily pulled out of the vertebrae. Also, at this alignment, the threaded grips 622,623 are opposing disc space. In the event that disc material has been removed due to a prior disectomy, there is no resistance acting on the threaded grips 622,623 to resist movement of the threaded fingers from the disc space. Even if disc material remains in residence in the disc space, the disc material yields to the threaded grips 622,623 as they are withdrawn from the disc space.

In FIG. 31, a relief 700 is shown between the threads 420 of the implant 400 and the threads 624 of the grips 622,623. The reliefs 700 provide an area in which waste material can accumulate and be expelled during the operation of inserting the combination of the distal end 606 and implant 400 into the bore between the disc space.

In order to securely hold the implant 400 within the distal end 606 of the tool 600, an insertion tool 800 shown in FIG. 32 is provided. The insertion tool 800 includes a shaft 802 sized to be received within the bore 608 of tool 600. The insert 800 has a threaded distal end 804 with a thread pattern to mate with the internal threads 504 at the trailing end 503 of implant 400. The proximal end of the insert 800 is provided with a knurled handle 806.

The distal end 804 is passed through the bore 608 and threaded onto threads 504 of the implant 400. The length of the shaft 802 is selected such that the handle 806 abuts handle 612 in a snug fit when the threads 804 are threaded onto an implant 400 contained within the distal end 606 in the alignment shown in FIG. 30. Accordingly, the first insert 800 ensures that the implant 400 is securely fastened in a nonmoving relation within the distal end 606 throughout the insertion of the implant 400 and the distal end 606 into the bore between the vertebrae.

After the implant has been placed in the full inserted position, the surgeon may simply then unthread the insert 800 from the implant and remove the insert 800 from the insertion tool 600. At this point, the insertion tool 600 may simply be pulled away from the spine with the grips 620–623 sliding past the implant 400 and with the implant 400 being retained in place in the desired implant location. However, from time to time due to hydrostatic forces and other factors, it may be difficult to simply pull the insertion tool 600 away from the implant 400. Accordingly, a second insert 900 (shown in FIG. 33) is provided.

The insert 900 extends from a proximal end 902 to a distal end 904 and has a shaft 906 therebetween. The shaft 906 is provided with threads 908 at the proximal end 902. The proximal end 902 is also provided with a handle 910. Distal end 904 is blunt and is sized to have a diameter greater than the diameter of the threaded opening 504 on the trailing end 503 of the implant 400. Accordingly, as a surgeon places the distal end 904 through bore 608 of tool 600 and abuts the implant 400 with the end 904, the surgeon can turn the handle 910 with the threads 908 received within threads 610 of the tool 600. As a result, the surgeon is urging the insertion tool 600 to separate from the implant 400 with sufficient force to overcome any hydrostatic forces or other forces otherwise resisting relative movement between the insertion tool 600 and the implant 400. Therefore, the second insert 900 may be used to pre-release the insert tool 600 from the implant 400 so that the insertion tool 600 may then be easily removed from the implant 400 after placing of the implant between the vertebrae.

Having disclosed the present invention of the preferred embodiment, it will be appreciated that the modifications and equivalents of the disclosed concepts which readily occur to one skilled in the art are intended to be included within the scope of the claims which are appended hereto.

What is claimed is:

1. An implant for use in spinal stabilization for placement into a disc space between two vertebra having end plates of cortical bone and a vertebra interior of cancellous bone, said implant comprising:

a plurality of generally linear thread segments;

rigid supports for holding said thread segments in spaced apart alignment;

said thread segments including a plurality of individual threads with said individual threads of said segments defining a thread pattern;

said supports and said thread segments defining a hollow implant interior exposed to an exterior of said implant.

2. The implant according to claim 1 wherein said thread segments are disposed in parallel alignment.

3. The implant according to claim 2 wherein said thread segments are supported for said segments to define longitudinal edges of a parallelepiped.

4. The implant according to claim 1 wherein said thread segments include first and second upper segments and first and second lower segments;

said first upper segment and said first lower segment joined in parallel spaced alignment by rigid supports extending perpendicularly therebetween;

said second upper segment and said second lower segment joined in parallel spaced alignment by rigid supports extending perpendicularly therebetween.

5. The implant according to claim 4 wherein said first and second upper segments are joined in parallel spaced alignment by rigid supports and wherein said first and second lower segments are joined in parallel spaced alignment by rigid supports.

6. The implant according to claim 5 wherein said rigid supports joining said first and second upper segments are convex and wherein said rigid supports joining said first and second lower segments are convex.

7. The implant according to claim 5 wherein said rigid supports joining said first and second upper segments and said rigid supports joining said first and second lower segments are spaced apart to define openings in communication with said implant interior.

8. The implant according to claim 1 wherein said implant is sized for said thread segments to reside in said cortical bone of said vertebra when said implant is placed within said bore.

9. A combination insertion tool and implant for fusing two opposing vertebra each having opposing end plates of cortical bone and vertebra interior of cancellous bone and wherein said opposing end plates are separated by a disc space, said combination comprising:

a. an implant having:
 1. at least four generally linear thread segments;
 2. rigid supports for holding said thread segments in spaced apart alignment with said thread segments defining longitudinal edges of a parallelepiped;
 3. said thread segments including a plurality of individual threads with said individual threads of said segments defining a thread pattern selected to mate with a thread pattern of said bore;
 4. said supports and said thread segments defining a hollow implant interior exposed to an exterior of said implant through at least aligned bone-growth openings formed through said implant on opposite sides thereof;

b. an insertion tool having:
 1. a distal end including grips sized to extend between opposing thread segments of said implant with at least two of said grips having external threads selected to match said thread pattern;
 2. a proximal end connected to said distal end through a tool body.

10. The combination according to claim 9 wherein said body has a tool bore formed therethrough from said proximal end to said distal end;

an insert having a threaded distal end and sized to be inserted through said tool body;

said implant including a threaded end to mate with said threaded distal end to removable secure said implant within said distal end of said insertion tool.

11. The combination according to claim 9 wherein said body has a tool bore formed therethrough from said proximal end to said distal end;

an insert having a distal end and sized to be inserted through said tool body to abut said implant held within said distal end of said insertion tool;

said insert and said insertion tool threadedly coupled for said insert to urge said implant out of said distal end of said insertion tool upon threading said insert and said insertion tool together.

12. A method for fusing two opposing vertebra each having opposing end plates of cortical bone and vertebra interior of cancellous bone and wherein said opposing end plates are separated by a disc space, said method comprising:

a. forming a threaded bore into said disc space and at least partially into said cortical bone of said opposing end plates;

b. selecting an implant having:
 1. at least four generally linear thread segments;
 2. rigid supports for holding said thread segments in spaced apart alignment with said thread segments defining longitudinal edges of a parallelepiped;
 3. said thread segments including a plurality of individual threads with said individual threads of said segments defining a thread pattern selected to mate with a thread pattern of said bore;
 4. said supports and said thread segments defining a hollow implant interior exposed to an exterior of said implant through at least aligned bone-growth openings formed through said implant on opposite sides thereof;

c. threading said implant into said bore to a full inserted position with said thread segments in residence in said cortical bone and with said bone-growth openings opposing said cancellous bone of each of said vertebra.

13. The method according to claim 12 comprising retaining said implant in an insertion tool having a distal end including grips sized to extend between opposing thread segments of said implant with at least two of said grips having external threads selected match said thread pattern and a proximal end connected to said distal end through a tool body, holding said implant with said insertion tool during said threading and threading until said grips oppose said disc space at said full inserted position.

* * * * *